United States Patent
Frantzen

Patent Number: 5,868,782
Date of Patent: Feb. 9, 1999

[54] RADIALLY EXPANDABLE AXIALLY NON-CONTRACTING SURGICAL STENT

[75] Inventor: John J. Frantzen, Copperopolis, Calif.

[73] Assignee: Global Therapeutics, Inc., Broomfield, Colo.

[21] Appl. No.: 773,102

[22] Filed: Dec. 24, 1996

[51] Int. Cl.[6] ............................. A61M 29/00; A61F 2/06
[52] U.S. Cl. ............................. 606/198; 606/1; 606/108; 606/191; 606/194; 606/200; 623/1; 623/12; 128/899
[58] Field of Search ............................. 606/1, 108, 191, 606/194, 198, 200; 623/1, 12; 128/899

[56] References Cited

U.S. PATENT DOCUMENTS

| | | |
|---|---|---|
| 5,133,732 | 7/1992 | Wiktor . |
| 5,139,480 | 8/1992 | Hickle et al. . |
| 5,195,984 | 3/1993 | Schatz . |
| 5,242,399 | 9/1993 | Lau et al. . |
| 5,314,444 | 5/1994 | Gianturco . |
| 5,421,955 | 6/1995 | Lau et al. . |
| 5,425,739 | 6/1995 | Jessen . |
| 5,441,515 | 8/1995 | Khosravi et al. . |
| 5,443,477 | 8/1995 | Marin et al. . |
| 5,494,029 | 2/1996 | Lane et al. . |
| 5,496,277 | 3/1996 | Termin et al. . |
| 5,507,767 | 4/1996 | Maeda et al. . |
| 5,507,771 | 4/1996 | Gianturco . |
| 5,514,154 | 5/1996 | Lau et al. . |
| 5,522,882 | 6/1996 | Gaterud et al. . |
| 5,531,741 | 7/1996 | Barbacci . |
| 5,549,662 | 8/1996 | Fordenbacher . |
| 5,603,721 | 2/1997 | Lau et al. ............................. 606/195 |
| 5,632,760 | 5/1997 | Sheiban et al. ............................. 606/195 |

FOREIGN PATENT DOCUMENTS

953027083  11/1995  European Pat. Off. .

Primary Examiner—William Lewis
Attorney, Agent, or Firm—Heisler & Associates

[57] ABSTRACT

A surgical stent (10) is provided which can be radially expanded away from a central axis (2) within a body lumen, such as an artery. The stent (10) is formed from a series of struts (20) circumscribing a cylindrical contour of the stent (10). Each strut (20) has a series of bends (30) formed therein with each bend including at least one trough (32) and at least one crest (36). Gaps (40) are provided between adjacent struts (20). Each gap (40) is spanned by an axial element such as a tie bar (50). Each tie bar (50) attaches to adjacent struts (20) through troughs (32) so that when the stent (10) is radially expanded, the struts (20) are not drawn together, but rather maintain their position and the stent (10) hence maintains its axial length without contracting. Other elements can alternatively be provided between adjacent circumferential elements to provide varying degrees of flexibility between adjacent struts (20).

19 Claims, 6 Drawing Sheets

RADIALLY EXPANDABLE AXIALLY NON-CONTRACTING SURGICAL STENT

FIELD OF THE INVENTION

The following invention relates to surgical stents of a generally cylindrical configuration which can be surgically implanted into a body lumen, such as an artery, and radially expanded. More specifically, this invention relates to radially expandable surgical stents which exhibit little or no axial contraction when radially expanded.

BACKGROUND OF THE INVENTION

Surgical stent have been known which can be surgically implanted into a body lumen, such as an artery, to reinforce, support, repair or otherwise enhance the performance of the lumen. For instance, in cardiovascular surgery it is often desirable to place a stent in the coronary artery at a location where the artery is damaged or is susceptible to collapse. The stent, once in place, reinforces that portion of the artery allowing normal blood flow to occur through the artery. One form of stent which is particularly desirable for implantation in arteries and other body lumens is a cylindrical stent which can be radially expanded from a first smaller diameter to a second larger diameter. Such radially expandable stents can be inserted into the artery by being located on a catheter and fed internally through the arterial pathways of the patient until the unexpanded stent is located where desired. The catheter is fitted with a balloon or other expansion mechanism which exerts a radial pressure outward on the stent causing the stent to expand radially to a larger diameter. Such expandable stents exhibit sufficient rigidity after being expanded that they will remain expanded after the catheter has been removed.

Radially expandable stents come in a variety of different configurations to provide optimal performance to various different particular circumstances. For instance, the patents to Lau (U.S. Pat. Nos. 5,514,154, 5,421,955, and 5,242,399), Baracci (U.S. Pat. No. 5,531,741), Gaterud (U.S. Pat. No. 5,522,882), Gianturco (U.S. Pat. Nos. 5,507,771 and 5,314,444), Termin (U.S. Pat. No. 5,496,277), Lane (U.S. Pat. No. 5,494,029), Maeda (U.S. Pat. No. 5,507,767), Marin (U.S. Pat. No. 5,443,477), Khosravi (U.S. Pat. No. 5,441,515), Jessen (U.S. Pat. No. 5,425,739), Hickle (U.S. Pat. No. 5,139,480), Schatz (U.S. Pat. No. 5,195,984), Fordenbacher (U.S. Pat. No. 5,549,662) and Wiktor (U.S. Pat. No. 5,133,732), each include some form of radially expandable stent for implantation into a body lumen.

Each of these prior art stents suffer from a variety of drawbacks which make them less than ideal. For instance, many of these expandable stents are not particularly flexible and they have a central axis which remains substantially linear when the stents are not yet expanded. Such lack of flexibility makes the stent difficult to thread along arterial pathways for proper positioning within the body of the patient. Another problem which is exhibited by each of these prior art stents is that when they are expanded radially, an axial length of these stents is decreased. Even the patent to Lau (U.S. Pat. No. 5,514,154), although it teaches a stent design which attempts to limit axial contraction, still exhibits some axial contraction, especially at one end thereof.

When a surgeon is positioning a stent within an artery or other body lumen, it is critical that the stent be positioned precisely where the surgeon desires the stent to be placed. A common occurrence with prior art stents is that the stent will be precisely located where desired before radial expansion and then when the stent is expanded, its axial contraction will cause the stent to not be finally located precisely where desired. Such a mis-location problem is compounded by the fact that most stents can only be easily expanded and not easily contracted once expansion has occurred.

Additionally, it is often difficult, even with state of the art medical imaging equipment, to accurately determine the location of a stent during implantation thereof within a body lumen. This difficulty in determining exactly what the position is of the stent compounds the problem of accurately locating the stent where desired. Accordingly, a need exists for a radially expandable stent which exhibits little or no axial contraction when radially expanded and which can be easily located by medical imaging equipment during the stent positioning process.

SUMMARY OF THE INVENTION

This invention provides a radially expandable stent which exhibits little or no contraction along an entire axial length thereof when the stent is expanded radially. The stent includes a series of struts which act as circumferential elements circumscribing the cylindrical contour of the stent. Each strut is aligned within a separate plane perpendicular to a central axis of the cylindrical contour of the stent and parallel to other planes of adjacent struts. The stent can have various different numbers of struts joined together to form the stent. However, at least two end struts are provided including a first end strut and a second end strut which define ends of the cylindrical contour of the stent. Intermediate struts are also typically provided between the two end struts.

Each of these struts exhibits a wave-like contour as they circumscribe the cylindrical contour of the stent. Thus, each strut has a series of bends which have troughs and crests alternating along the length of each strut. Each trough defines a portion of the strut which is most distant from adjacent struts and each crest defines a portion of the strut closest to adjacent struts. An amplitude of each strut, defined by the distance between the bottom of each trough and the top of each crest is modified when the stent is radially expanded so that the amplitude is generally decreased.

The end struts are attached to adjacent intermediate struts by tie bars which act as axial elements connecting the two adjacent struts together. Tie bars can also connect adjacent intermediate struts to each other. Each tie bar attaches to the struts adjacent thereto through a first junction on one extremity of the tie bar and a second junction on an opposite extremity of the tie bar. Both the first junction and the second junction are located within troughs of the struts. Thus, the tie bars span a gap between adjacent struts at a maximum width portion of the gap. Not all of the gaps are necessarily spanned by tie bar axial elements. Rather, separate intermediate circumferential elements can be attached to each other through links which connect to the intermediate elements at locations spaced away from the troughs thereof. Depending on the flexibility needs for the stent, different numbers of troughs can be provided with tie bars attaching adjacent struts to each other. If enhanced flexibility is desired, a greater number of troughs will be left empty with as few as one tie bar located between adjacent struts. The undulating contour of the struts can either be serpentine with the struts lacking flat surfaces but rather curving entirely along their length, or the struts can be formed from a series of linear sections including linear trough sections and linear crest sections joined together by linear inflection sections.

To enhance the visibility of the stent when viewed by various different medical imaging devices, the struts forming the first end and the second end of the stent can be formed from a radio-opaque material, such as gold, silver or platinum which will allow the first end and second end of the stent to be clearly visible through a medical imaging device during or after implantation of the stent within a body lumen of a patient.

OBJECTS OF THE INVENTION

Accordingly, a primary object of the present invention is to provide a radially expandable stent which does not contract axially when expanded radially.

Another object of the present invention is to provide a stent which exhibits sufficient flexibility to allow a central axis thereof to bend, especially when the stent is being threaded through arterial pathways within a patient.

Another object of the present invention is to provide a surgical stent which exhibits little or no axial contraction at ends thereof when expanded radially.

Another object of the present invention is to provide a surgical stent which has ends thereof formed from a radio-opaque material which can be easily viewed by a medical imaging device.

Another object of the present invention is to provide a surgical stent which is formed from a series of struts which form circumferential elements circumscribing a cylindrical contour of the stent, the individual struts joined together by tie bars which act as axial elements restraining the struts from contracting together when expanded radially.

Another object of the present invention is to provide a surgical stent which has a configuration which lends itself to manufacture from a variety of techniques including machining, photo-etching and other precision low cost techniques.

Another object of the present invention is to provide a surgical stent which has a configuration which exhibits the strength necessary to support a body lumen when implanted therein and radially expanded.

Another object of the present invention is to provide a surgical stent which can be located within a body lumen by a surgeon with a high degree of locational precision.

Other further objects of the present invention will become apparent from a careful reading of the included description and claims and from a review of the drawing figures.

DESCRIPTION OF THE PREFERRED EMBODIMENT

Figure 1:
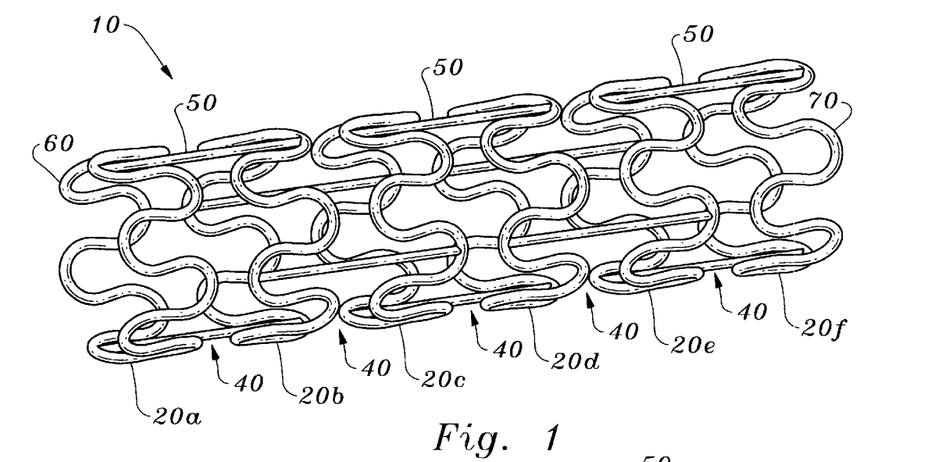
FIG. 1 is a perspective view of a preferred embodiment of the surgical stent of this invention before radial expansion occurs.
Figure 2:
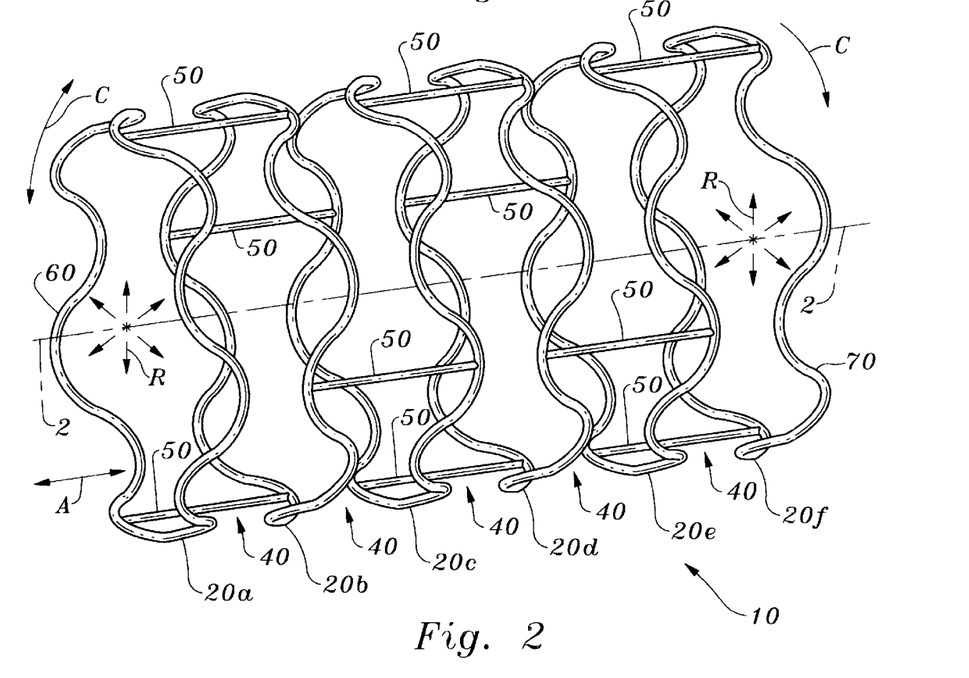
FIG. 2 is a perspective view of the stent which is shown in FIG. 1 after radial expansion has occurred.

Referring to the drawings, wherein like reference numerals represent like parts throughout the various drawing figures, reference numeral 10 is directed to a radially expandable axially non-contracting surgical stent (FIGS. 1 and 2). The stent 10 generally exhibits a cylindrical contour defined by a series of circumferential elements, referred to as struts 20, tied together by multiple axial elements, many of which are referred to as tie bars 50. The struts 20 are generally wave-like in form such that an amplitude 22 (FIG. 4) of the struts 20 can be decreased and a diameter of the struts 20 increased, as the diameter of the stent 10 is radially expanded.

In essence, and with particular reference to FIGS. 1 and 2, the stent 10 includes the following basic features. A series of circumferential elements such as struts 20a, 20b, 20c, 20d, 20e, 20f are each oriented in a manner circumscribing the cylindrical contour of the stent 10. Each strut 20 includes a series of bends 30 (FIGS. 3 and 4) providing the strut 20 with its wave-like form. Each strut 20 is spaced from adjacent struts 20 by a gap 40 there between. A series of tie bars 50 extend between adjacent struts 20, and across the gap 40, connecting the adjacent struts 20 to each other. The tie bars 50 act as axial elements maintaining the axial position of the struts 20 during radial expansion of the stent 10 along arrow R (FIG. 2). The tie bars 50 are sufficiently flexible and spaced sufficiently apart from other tie bars 50 that the entire stent 10 can flex somewhat causing the central axis 2 to bend as the stent 10 is moved through arterial pathways or other body lumens before radial expansion of the stent 10.

More specifically, and with particular reference to FIGS. 1 through 4, details of the surgical stent 10 are specifically provided. Each strut 20 preferably is a thin elongate strand of material such as metal which is confined to lie substantially within a cylindrical contour forming the stent 10. Each strut 20 exhibits a wave-like contour having a constant amplitude 22 (FIG. 4) and wavelength 24 (FIG. 4) as it circumscribes the cylindrical contour of the stent 10. Each strut 20 thus has bends 30 therein which provide a series of alternating troughs 32 and crests 36. Between each adjacent trough 32 and crest 36 an inflection point 34 is provided which defines a transition between the trough 32 and the crest 36.

Figure 3:
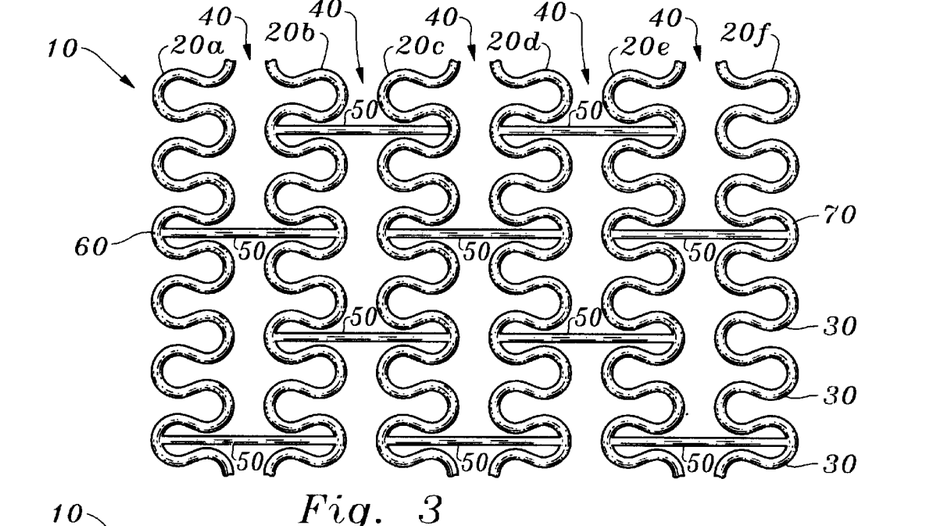
FIG. 3 is a top plan view of that which is shown in FIG. 1 after cylindrical projection of the stent onto a planar surface to reveal details of the configuration of the stent.
Figure 4:
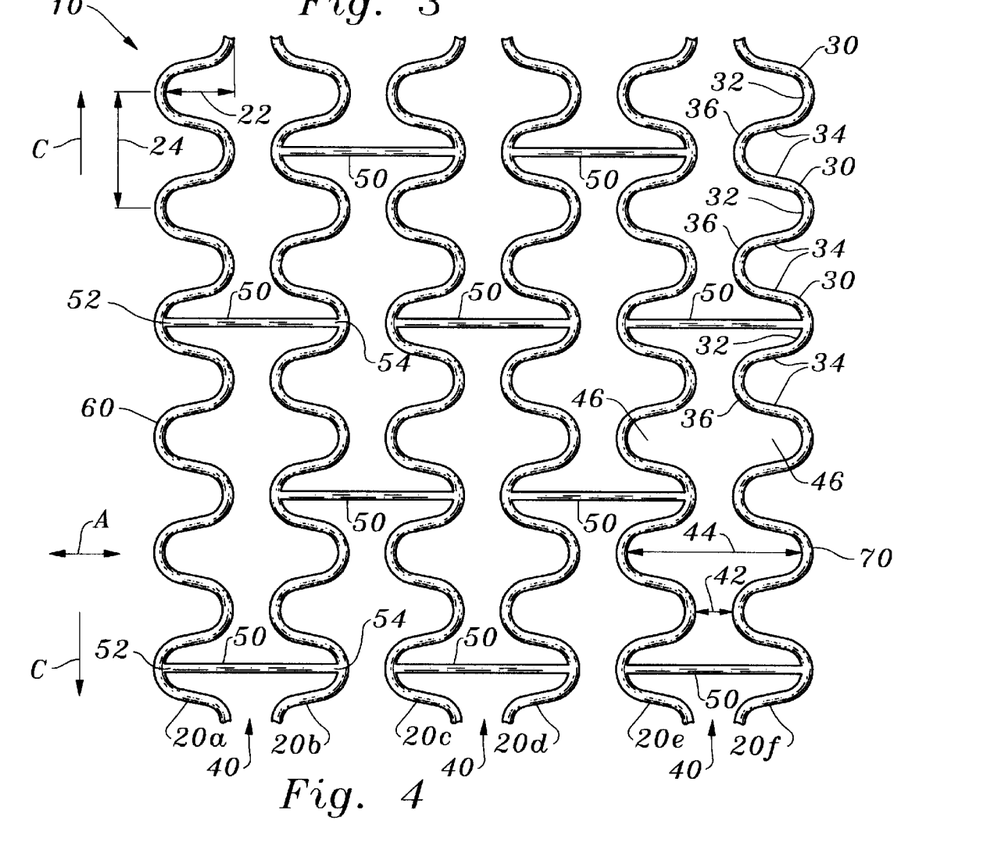
FIG. 4 is a top plan view of the stent which is shown in FIG. 2 after cylindrical projection of the stent onto a planar surface to reveal details of the configuration of the stent after radial expansion.

Whether a portion of a bend 30 is a trough 32 or a crest 36 is largely a matter of perspective. For consistency, the trough 32 shall be identified as that portion of each bend 30 which is most distant from the adjacent strut 20 that the bend 30 is facing, and the crest 36 is that portion of each bend 30 which is closest to the adjacent strut 20 that the bend 30 is facing. Each trough 32 and crest 36 is not a particular point on each bend 30, but rather is a region extending from one inflection point 34 to the next adjacent inflection point 34 along each strut 20. Whether a portion of a bend 30 is a trough 32 or a crest 36 also depends on the side of each bend 30 that is being analyzed. For example, a bend 30 spaced from a first end 60 and a second end 70 of the stent 10 can have a crest 36 on one side of the bend 30 closest to the first end 60 and a trough 32 on the other side of the same bend 30 closest to the second end 70.

Each inflection point 34 is the point at which the bend 30 transitions from curving in one direction (i.e. in a clockwise direction) to curving in an opposite direction (i.e. a counterclockwise direction). Each inflection point 34 is preferably a single point which occurs at the beginning and a middle of each wavelength 24 of each strut 20. However, the inflection point 34 can alternatively be a linear region between each crest 36 and each trough 32, rather than merely a point. Preferably, each strut 20 is aligned with adjacent struts 20 so that the troughs 32 of adjacent struts 20 are axially aligned with each other and the crests 36 of each strut 20 are axially aligned with each other.

A gap 40 is located between each pair of adjacent struts 20. Thus, end struts 20 such as the strut 20a adjacent the first end 60 and the strut 20f adjacent the second end 70 have only one gap 40 adjacent thereto and intermediate struts 20b, 20c, 20d, 20e have gaps 40 on either side. Preferably, each gap 40 defines a space between adjacent struts 20 which is not crossed by either strut 20 which is adjacent each gap 40. Rather, the tie bars 50, described in detail below, are provided to span the gaps 40.

Each gap 40 has a width which varies depending on whether the gap 40 location is adjacent troughs 32 of adjacent struts 20 or crests 36 of adjacent struts 20. At locations on the gap 40 adjacent to the crests 36 of adjacent struts 20, a minimum width 42 in the gap 40 is defined (FIG. 4). At locations along the gap 40 adjacent the troughs 32 of adjacent struts 20, a maximum width 44 in the gap 40 is defined (FIG. 4). Each gap 40 thus exhibits an alternating pattern of minimums 42 and maximums 44 as the gap 40 circumscribes the cylindrical contour of the stent 10.

Each maximum 44 also defines a lateral slot 46 (FIG. 4) where the gap 40 extends a significant distance away from a central plane of the gap 40 and toward adjacent struts 20. The slot 46 has a contour which is defined by the configuration of the bends 30 of adjacent struts 20 and the radial expansion status of the stent 10 (i.e. before radial expansion along arrow R of FIG. 2 or after radial expansion). Preferably, before radial expansion along arrow R (FIG. 2), each slot 46 (FIG. 4) has a bulbous contour (FIG. 3) which mirrors a bulbous contour of the bends 30 such that the slot 46 first narrows and then expands as the slot 46 extends away from a center plane of the gap 40 and down into one of the troughs 32 in one of the bends 30 of an adjacent strut 20. After the stent 10 has been radially expanded (FIG. 4), the slots 46 lose this bulbous character and rather have a contour which tapers in width as the slots 46 extend away from a central plane of the gap 40.

By configuring the struts 20 to have this characteristic of bends 30 with a bulbous contour, providing the slots 46 with a narrowing and then expanding width, the struts 20 are allowed to expand further radially, along arrow R. This allows the stent 10 to extend to a greater length circumferentially, along arrow C (FIGS. 2 and 4), maximizing radial expandability thereof. This bulbous contour of the slots 46 also tends to allow the amplitude 22 (FIG. 4) of the struts 20 to remain unchanged during initial expansion of the stent 10 radially. Only after significant radial expansion and circumferential elongation does the amplitude 22 of the struts 20 begin to significantly decrease.

At least one tie bar 50 is oriented within each gap 40. The tie bar 50 is preferably a thin elongate structure having a first extremity spaced from a second extremity. The first extremity attaches to a first adjacent strut 20 at a first junction 52 and the second extremity attaches to a second adjacent strut 20 at a second junction 54. The first junction 52 and second junction 54 are both preferably located within troughs 32 of the struts 20 which are adjacent the gap 40 that is spanned by the tie bar 50.

To prevent axial contraction along arrow A (FIG. 2) during radial expansion of the stent 10, it is important that at least the extremities of the tie bar 50 which connect to end struts 20a, 20f adjacent the first end 60 and the second end 70 attach to troughs 32 of the end struts 20a, 20f. The second extremities of the tie bar 50 which connect to intermediate struts 20 spaced from the first end 60 and the second end 70 can either be attached within troughs 32 or crests 36.

With at least one tie bar 50 in place across each gap 40 and with the junctions 52, 54 located in troughs 32, the length of the slots 46 in the gap 40 are maintained. Thus, when the stent 10 is radially expanded along arrow R to the point where the amplitude 22 of the struts 20 adjacent each gap 40 begins to decrease, the struts 20 adjacent each gap 40 are not contracted together. Rather, the minimums 42 in the gaps 40 are enlarged and the struts 20, and particularly the end struts 20a, 20f maintain their position. Hence, no axial contraction along arrow A occurs.

Of primary importance in configuring the stent 10 is that gaps 40 adjacent the first end 60 and second end 70 be spanned by tie bars 50 which attach within troughs 32 in the struts 20a, 20f defining the first end 60 and the second end 70. Additionally, the other tie bars 50 between intermediate struts 20b, 20c, 20d, 20e can either be located in troughs 32 or at crests 36. However, the tie bars 50 between adjacent intermediate struts 20b, 20c, 20d, 20e should attach to at least an equal number of troughs 32 and crests 36 if not a greater number of troughs 32, as shown in FIGS. 1–4 where tie bars 50 only attach to troughs 32. It has been determined from experience that the thin cross sections of the tie bars 50 cause the tie bars 50 to bend somewhat in many cases. Thus, it is beneficial to have a greater number of gaps 40 spanned by tie bars 50 which connect to adjacent struts 20 at troughs 32 thereof than tie bars 50 which attach to crests 36 thereof, to compensate for the possibility of flexing of the tie bars 50.

Preferably, each gap 40 is provided with tie bars 50 which extend from troughs 34 of each adjacent strut 20. While in theory such a configuration could actually cause the stent 10 to expand axially along arrow A when expanded radially along arrow R, the tie bars 50 bend somewhat when located within a body lumen and hence are slightly shortened, causing the stent 10 to in reality remain substantially the same axial length as before expansion, with only the slight possibility of a minimal amount of either contraction or expansion. For reference, it is noted that even so called non-contracting stents, such as the expandable stent taught by Lau (U.S. Pat. No. 5,514,154), can contract as much as one half of the amplitude of circumferential elements forming such prior art stents. This contraction of prior art stents such as that taught by Lau particularly occurs at ends of the stents where axial elements join circumferential elements at crests in the circumferential elements.

The material forming the struts 20 and other elements of the stent 10 are preferably made of a stainless steel having a sufficiently minimal cross section that the struts 20 can be easily loaded with radial force, such as along arrow R (FIG. 2), to a point exceeding the elastic limit of the material forming the struts 20. When such a radial force is applied, the material forming the struts 20 is plastically deformed, causing the struts 20 to expand radially, elongate circumferentially and contract in amplitude. Such deformation of the material forming the struts 20 could in theory occur until the struts 20 were deformed into the shape of a circle before additional deformation would eventually cause failure of the struts 20 in tension.

In practice however, the stent 10 is provided with overall structural strength by not expanding the stent 10 to its maximum possible amount, but rather to a point where the struts 20 still exhibit a wave-like appearance with the amplitude only slightly decreased and the wave length of the struts 20 magnified by a similar amount to the amount of magnification in the circumferential length of each strut 20. Although the struts 20 have undergone plastic deformation, the ultimate strength of the material forming the struts 20 has not been exceeded. Thus, the material still exhibits similar characteristics as far as strength is concerned and can provide the desired function of supporting a body lumen in its expanded configuration.

It is noted that stainless steel has a yield strength of between 40,000 and 75,000 pounds per square inch and an ultimate strength of between 90,000 and 125,000 pounds per square inch. Thus, it is relatively straight forward to provide sufficient radial force on the stent 10 to cause the material forming the struts 20 to have its yield strength exceeded but to not have its ultimate strength exceeded. This is especially true in that the struts 20 are actually "bending" and not "stretching" during the radial expansion process. Techniques for expanding stents such as the stent 10 are well known in the art. One such technique involves placing an expandable balloon within the stent which can be filled with air or other fluid, causing the balloon to elastically expand and exert a radial force on the stent. Specific details of such expansion techniques are articulated in the patents cited in the background of the invention and are incorporated herein by reference.

As an alternative to the surgical stent 10 of the preferred embodiment, a surgical stent 110 (FIGS. 5 and 6) is provided featuring links 180 spanning certain of the portions of the stent 110. The stent 110 is similar in configuration to the stent 10 of the preferred embodiment except as specifically identified below. Thus, the stent 110 includes struts 120 which provide circumferential elements for the stent 110 with bends 130 similar to the bends 30 in the struts 20 of the preferred embodiment and gaps 140 between adjacent struts 120. Each bend 130 includes a series of alternating troughs 132 and crests 136. Tie bars 150 similar to the tie bars 50 of the preferred embodiment are interposed across some of the gaps 140, while other gaps 140 are provided with the links 180. Preferably, the gaps 140 adjacent the first end 160 and the second end 170 are provided with tie bars 150 therein. In addition, these tie bars 150 are preferably oriented between troughs 132 of adjacent struts 120. Other gaps 140 spaced away from the first end 160 and second end 170 can either include tie bars 150 or links 180.

Each link 180 is a thin elongate structure having a left end 182 (FIG. 6), a right end 184 and an elbow 186 located medially between the left end 182 and the right end 184. Thus, the link 180 is provided with a left arm 187 extending from the left end 182 to the elbow 186 and a right arm 188 extending from the right end 184 to the elbow 186. Preferably, the elbow 186 causes the left arm 187 to be perpendicular to the right arm 188. The elbow 186 provides a particular location where the left arm 187 and right arm 188 of each link 180 can flex toward or away from each other about arrow F (FIG. 6) in a manner facilitating flexibility for the entire stent 110 when being threaded through arterial pathways.

Figure 5:
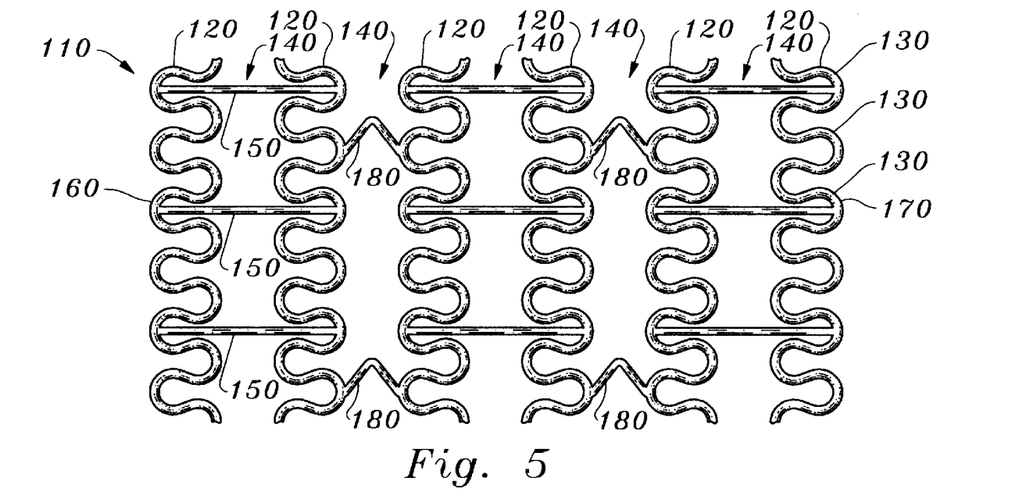
FIG. 5 is a top plan view of a stent forming a first alternative embodiment of that which is shown in FIG. 3, before radial expansion.
Figure 6:
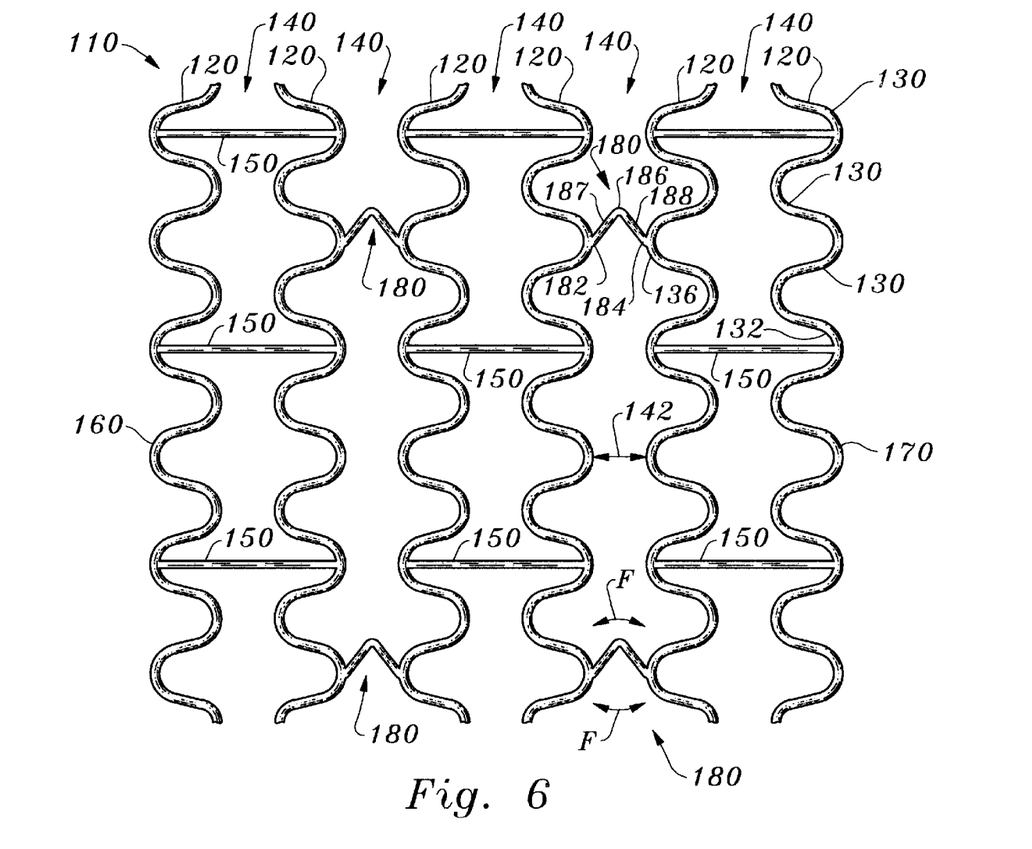
FIG. 6 is a top plan view of the stent which is shown in FIG. 5 after radial expansion has occurred.

The links 180 are preferably oriented at minimums 142 in the gap 140 in which the links 180 are located. Preferably, gaps 140 having the links 180 located therein alternate with gaps 140 having the tie bars 150 located therein and do not include gaps 140 adjacent the first end 160 and second end 170. When the stent 110 is expanded radially, and an amplitude of the bends 130 and the struts 120 is decreased, the links 180 will hold crests 136 of adjacent struts 120 together across the gaps 140. This will tend to have a contraction effect on the stent 110. However, the tie bars 150 being interposed between troughs 132 and adjacent struts 120 will tend to have an expanding effect on the stent 110. The net result of the tie bars 150 providing an axially expanding effect and the links 180 providing an axially contracting effect is that the stent 110 is provided with no or minimal net contraction when the stent 110 is expanded radially.

Preferably, the gaps 140 having tie bars 150 therein are provided with three tie bars 150 and the struts 120 are provided with six troughs 132 and six crests 136 such that only half of the possible tie bar 150 locations are utilized. Preferably, the gaps 140 fitted with links 180 include only two links 180 therein. Thus, four minimums 142 are left vacant. The locations of the links 180 are preferably circumferentially offset with the locations of the tie bars 150 to further enhance flexibility of the stent 110.

Figure 7:
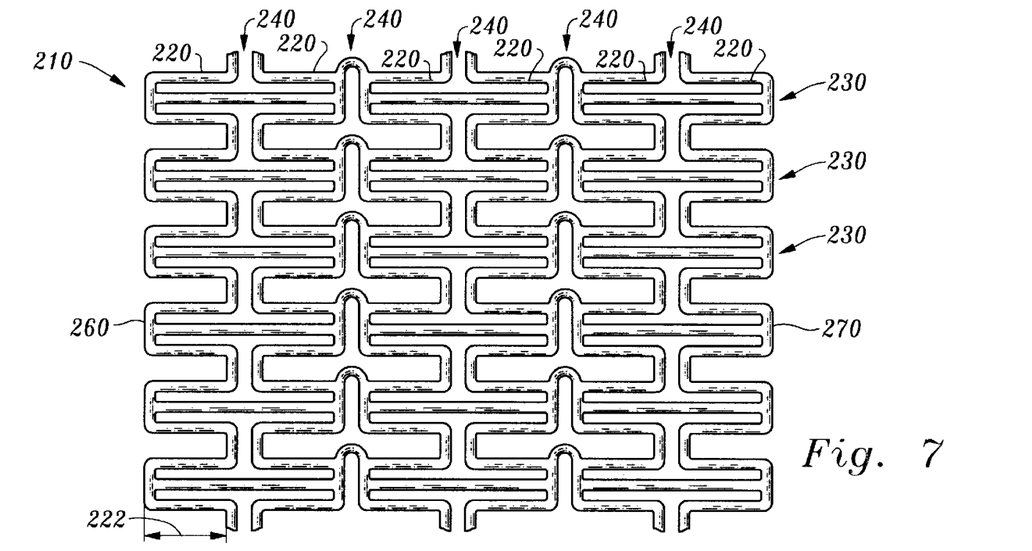
FIG. 7 is a top plan view of a stent forming a second alternative embodiment of that which is shown in FIG. 3, before radial expansion.
Figure 8:
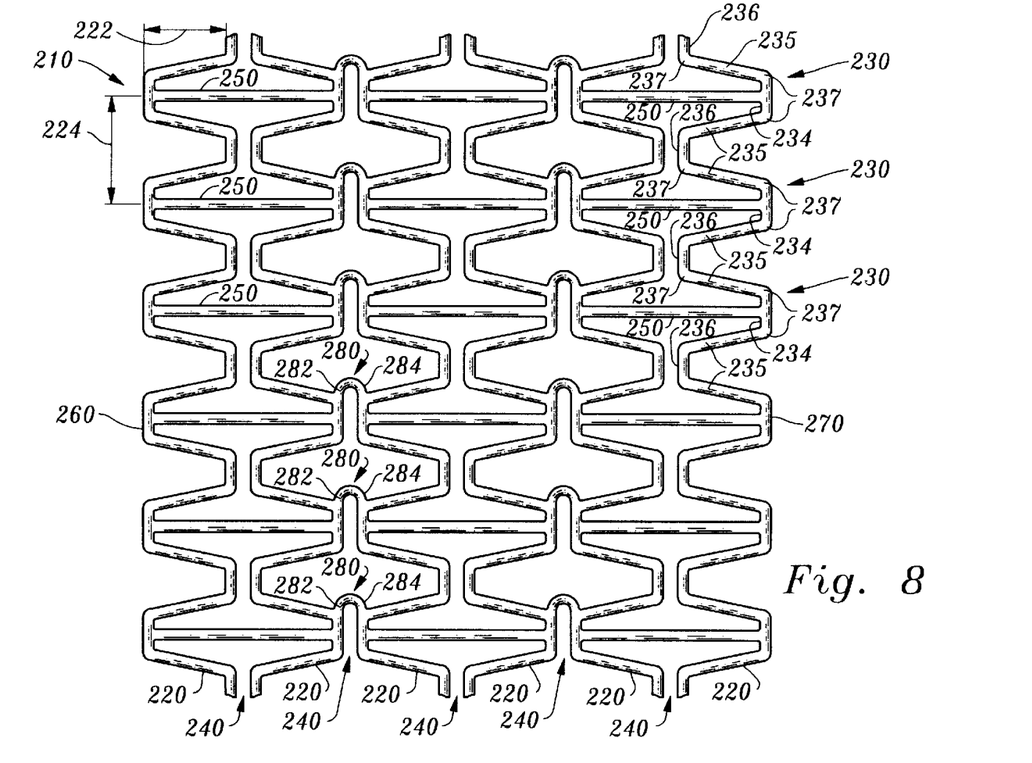
FIG. 8 is a top plan view of the stent which is shown in FIG. 7 after radial expansion has occurred.

With particular reference to FIGS. 7 and 8, details of a second alternative embodiment of the stent 10 featuring links and struts formed of individual linear segments is provided. Such a stent 210 still exhibits a cylindrical contour defined by a plurality of struts 220. Only those details of this stent 210 which differ from details of the stent 10 of the preferred embodiment will be provided in detail below. Each of the struts 220 has a wave-like appearance with a series of bends 230 located therein. However, each bend 230 is provided with a flat trough 234 (FIG. 8) parallel to and axially spaced from a plurality of flat crests 236. Each flat trough 234 and flat crest 236 is preferably oriented within a plane perpendicular to the central axis (see the central axis 2 of FIG. 2) of the stent 210.

Each flat trough 234 is connected to adjacent flat crests 236 by inflection legs 235. Each inflection leg 235 is preferably linear and is non-parallel with either the flat trough 234 or the flat crest 236. Corners 237 are provided at transitions between ends of the inflection legs 235 and adjacent flat troughs 234 and flat crests 236. The stent 210 expands radially in a similar manner to the stent 10 of the preferred embodiment except that the struts 220 are modified from a somewhat rectangular configuration for the bends 230 to a trapezoidal configuration for the bends 230. The amplitude 222 of the struts 220 is decreased when radial expansion occurs and the wave length 224 of the struts 220 is increased when radial expansion occurs in a manner similar to that exhibited by the stent 10 of the preferred embodiment.

Gaps 240 are oriented between adjacent struts 220 in the stent 210. Tie bars 250 are provided between flat troughs 234 in adjacent struts 220 and spanning the gaps 240. Such tie bars 250 are preferably located at the gaps 240 adjacent a first end 260 and a second end 270 and are optional at other gaps 240 in the stent 210.

As an alternative to the tie bars 250, the gaps 240 can be spanned by arched links 280 (FIG. 8). Preferably, each arched link 280 has a left end 282 spaced from a right end 284 and is bowed between the left end 282 and the right end 284. Preferably, the arched links 280 are interposed between adjacent flat crests 236 of struts 220 adjacent the gap 240 spanned by the arched link 280. The arched link 280 provides a similar function to that provided by the link 180 of the first alternative embodiment in that it joins adjacent gaps 240 to provide localized contraction to offset localized expansion caused by the tie bars 250 and allow the stent 210 as a whole to exhibit little if any contraction or expansion in the axial direction when radially expanded.

As an alternative to the strut 220, the arched links 280 can be replaced with links 180. Preferably in this embodiment, each flat trough 234 facing a gap 240 includes a tie bar 250 therein and each flat crest 236 adjacent a gap 240 including an arched link 280 attached thereto. Thus, no vacancies are provided in any of the flat troughs 234 or flat crests 236. In such a configuration, the stent 210 is provided with minimal flexibility for applications where radial strength is of primary importance and flexibility is of secondary importance. As an alternative, vacancies can be provided in the troughs 234 and the crests 236 in a manner similar to the preferred embodiment or the first alternative embodiment.

Figure 9:
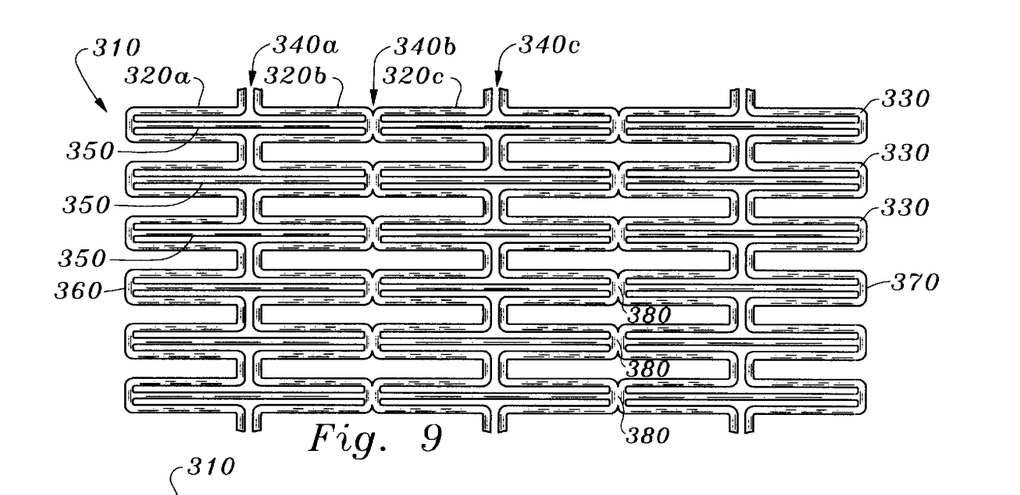
FIG. 9 is a top plan view of a stent forming a third alternative embodiment of that which is shown in FIG. 3, before radial expansion.
Figure 10:
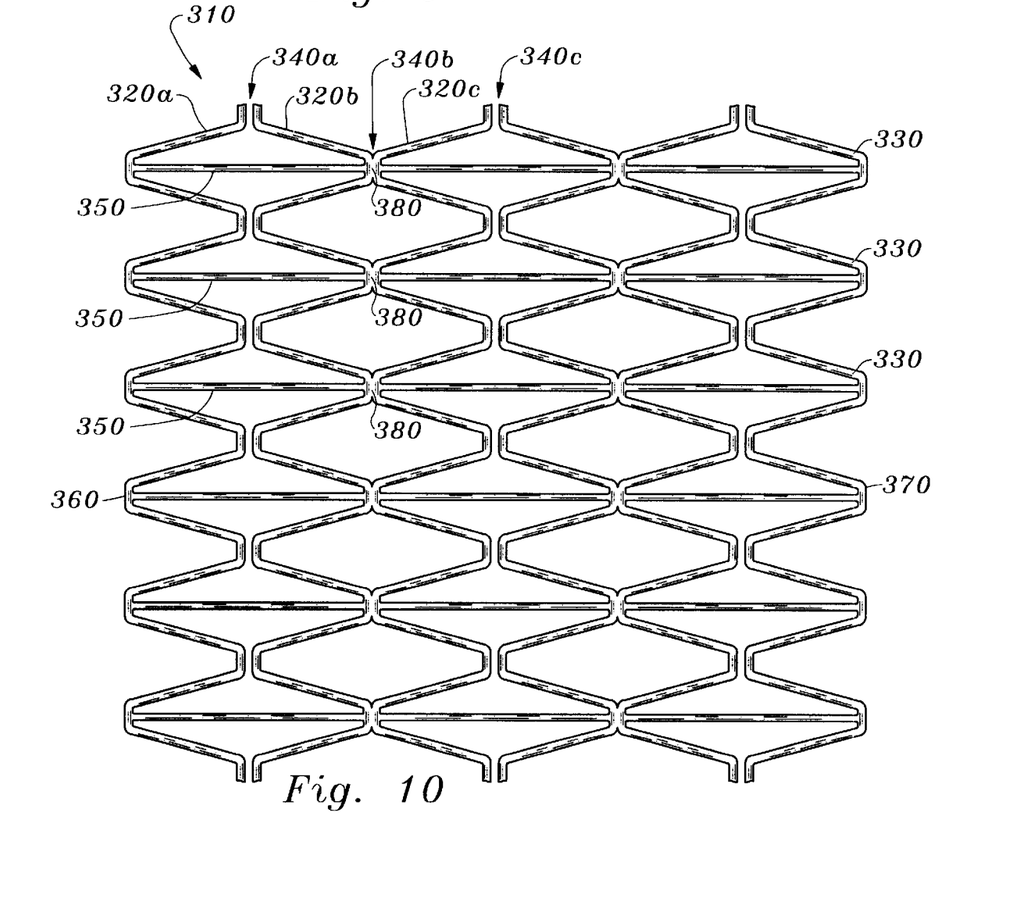
FIG. 10 is a top plan view of the stent which is shown in FIG. 9 after radial expansion has occurred.

With particular reference to FIGS. 9 and 10, details of a third alternative embodiment is provided of the surgical stent 10 of the preferred embodiment. This third alternative embodiment is for a stent 310 featuring multi-element junctions 380 therein. Details of the stent 310 are similar to those of the stent 210 except where particularly provided below. The stent 310 thus includes a series of struts 320 which circumscribe a cylindrical contour of the stent 310 and which exhibit a wave-like contour having bends 330. Gaps 340 are provided between adjacent struts 320. Alternating gaps 340, and particularly the gaps 340 adjacent the first end 360 and the second end 370 are fitted with tie bars 350 therein. Other gaps 340 can be fitted with either tie bars 350 or have a width thereof reduced to zero and have crests of struts 320 adjacent the gap 340 attached together at multi-element junctions 380.

In essence, the multi-element junction 380 replaces the arched link 280 of the second alternative embodiment and causes the gap 340 having multi-element junctions 380 therein to be reduced to a width of zero. The stent 310 is expandable in a manner similar to the stent 210. However, it is noted that because the tie bars 250 are aligned with the multi-element junctions 280, each of the individual tie bars 250 forms a continuous axial element extending from the first end 360 to the second end 370. Thus, an axial length of the stent 310 is maintained without contraction to a high degree of precision. The only possibility of axial contraction comes from any possible tie bar 350 bending, rather than the arrangement of the elements forming the stent 310. The tie bars 350 also provide a limited amount of flex for the stent 310. However, the stent 310 does not exhibit as much flexibility as the stents 10, 110, 210 of the other embodiments and is particularly suited for applications where flexibility is truly secondary and lack of axial contraction and radial strength are of primary importance.

Figure 11:
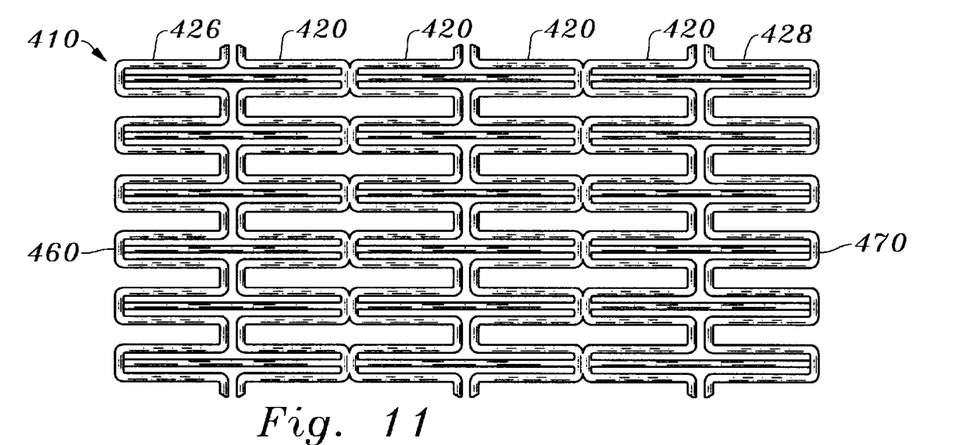
FIG. 11 is a top plan view of a stent forming an alternative embodiment to that which is shown in FIG. 9 with end struts thereof formed from a material having radio-opaque properties, before radial expansion.
Figure 12:
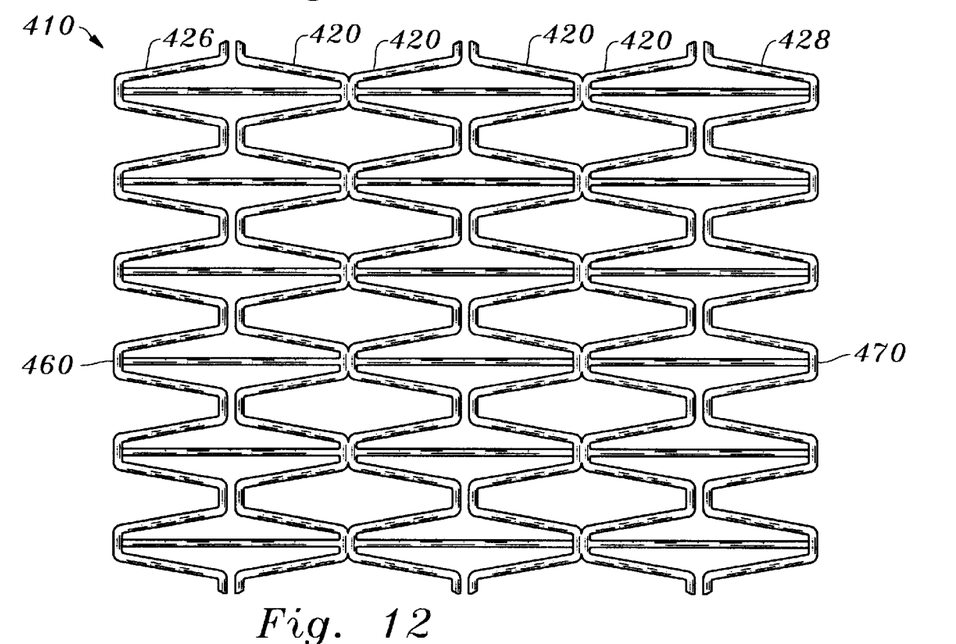
FIG. 12 is a top plan view of the stent which is shown in FIG. 11 after radial expansion thereof.
Figure 13:
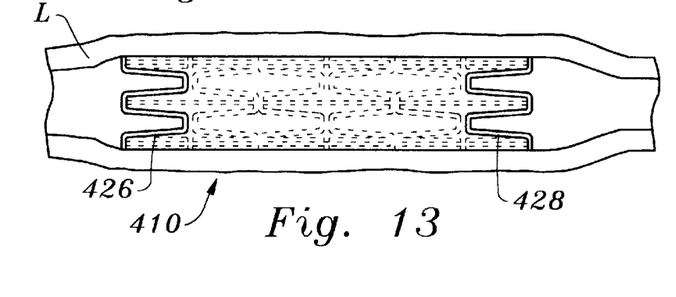
FIG. 13 is a front elevation view of the stent shown in FIGS. 11 and 12 as it would appear when viewed by a medical imaging device which more clearly discerns radio-opaque material than non-radio-opaque material, the lumen having been clearly outlined by a radio-opaque dye and portions of the stent formed from non-radio-opaque material shown in broken lines representing that they are only vaguely apparent.

With particular reference to FIGS. 11, 12 and 13, details of a fourth alternative embodiment are provided. The stent 410 is only described to the extent that details thereof are distinct from details of the stent 310 of the third alternative embodiment. The stent 410 thus includes a series of struts 420 circumscribing the cylindrical contour of the stent 410. A first end strut 426 is located adjacent the first end 460 and a second end strut 428 is located adjacent the second end 470. These end struts 426, 428 are formed from a unique material from the material forming the middle struts 420 and other elements of the stent 410. This use of a different material than the material forming other elements of the stent 410 for the end struts 426, 428 could be similarly incorporated into the other stents 10, 110, 210, 310 of the other embodiments in a similar manner.

The material forming the end struts 426, 428 is preferably a material exhibiting opacity when viewed by a medical imaging device to a greater extent than the material forming other portions of the stent 410. For instance, when stainless steel is utilized to form other portions of the stent 410, the end struts 426, 428 can be formed from a material such as gold, platinum, silver or some alloy or amalgam thereof, or other similar sufficiently dense material to provide a clear image when viewed by a medical imaging device.

The end struts 426, 428 are not namely plated with radio-opaque material. Rather the end struts 426, 428 are constructed out of the radio-opaque material. This is important because plating of stents, such as the stent 410, cause a thickness of elements forming the stents to be increased by a few thousandths of an inch. Such a plated stent then becomes difficult to maneuver through arterial pathways and other degradation in performance. Also, when end struts are thickened by plating, the radio-opaque material has a relatively broad profile that can be excessively bright when viewed with a fluoroscope or other medical imaging device, causing the stent's radio-opaque ends to appear blurry and not precisely defined. By forming the end struts 426, 428 entirely of radio-opaque material, the plating drawbacks are avoided.

As shown in FIG. 13, when the end struts 426, 428 are formed from a "radio-opaque" material, as described above, the ends 460, 470 of the stent 410 are clearly discernible when utilizing the medical imaging device. Additionally, the lumen L in which the stent 410 is located can be highlighted in a medical imaging device by coating the lumen L with a radio-opaque dye as is known in the art. A medical imaging device, such as an X-ray, can then be utilized to precisely determine the exact location of the stent 410 within the lumen L prior to or after expansion of the stent 410. Other portions of the stent 410 are either invisible when viewed with a medical imaging device or only vaguely discernible, as exhibited by FIG. 13 with broken lines. Preferably, the radio-opaque material forming the end struts 426, 428 is not merely a plating applied to the end struts 426, 428 but rather the end struts 426, 428 are formed entirely from the material selected.

In use and operation, and with particular reference to FIGS. 1, 2 and 13, details of the operation of the stents 10, 110, 210, 310, 410 are described. Initially, the stent 10 or alternative embodiment stents 110, 210, 310, 410 is provided in its non-radially expanded configuration as shown in FIG. 1. The stent is located at the desired position, utilizing prior art techniques such as catheterization, until the stent 10 is positioned where desired. The stent 10 is then expanded radially, along arrow R (FIG. 2), causing the wavelength 24 to increase, the amplitude 22 to decrease and the circumferential length (along arrow C of FIG. 2) to increase until the stent 10 is provided with the expanded diameter desired for the particular medical application. Because the stent 10 is configured as disclosed hereinabove and shown in the drawings, the first end 60 and second end 70 remain precisely positioned with respect to each other and with respect to the body lumen during the entire expansion process. Hence, little or no expansion or contraction of the stent 10 occurs.

When the stent 410 of the fourth alternative embodiment is utilized, the stent 410 is positioned as discussed above with respect to the preferred embodiment. However, before expansion of the stent 410 a radio-opaque dye is injected into the lumen involved and a medical imaging device, such as an X-ray machine, is utilized to verify that the stent 410 is positioned precisely where desired. If the position of the stent 410 is not precisely where desired, additional manipulation of the stent 410 can be done before expansion of the stent 410 has occurred. Once the medical professional is confident that the stent 410 is positioned where desired, the stent 410 is expanded as discussed above with respect to the preferred embodiment. Medical imaging devices can then be used immediately there after and on a follow-up basis to verify that the stent 410 is still in the desired position for maximum medical efficacy.

Moreover, having thus described the invention, it should be apparent that various different modifications could be made to the particular configuration of elements forming the stents 10, 110, 210, 310, 410 disclosed herein. For instance, while each of the embodiments disclosed herein reveals a series of six struts 20, 120, 220, 320, 420 a greater or lesser number could be provided depending on the particular needs of a specific surgical case. Additionally, while each strut 20, 120, 220, 320, 420 is provided with a series of six bends 30, 130, 230, 330 a greater or lesser number of bends 30, 130, 230, 330 could be provided so long as at least one bend is provided. While the different embodiments have featured different types and numbers of circumferential elements and axial elements, it is understood that many of these features could be utilized in other embodiments than those where such features are specifically shown. For instance, multi-element junctions such as the junctions 380 could be used to join together adjacent crests 36 of the struts 20 of the stent 10 of the preferred embodiment. Similarly, the stent 10 of the preferred embodiment could be provided with tie bars 50 located in every slot 46.

What is claimed is:

1. A radially expandable axially substantially non-contracting stent for surgical implantation into a body lumen, such as an artery, said stent having a generally cylindrical contour both before and after expansion thereof, said stent comprising in combination:

at least three circumferential elements, each circumferential element forming an elongate circuit completely circumscribing said cylindrical contour, a first one of said circumferential elements defining a first end of said stent, a second one of second circumferential elements defining a second end of said stent;

each said circumferential element having a wave-like series of bends therein as each said circumferential element circumscribes said cylindrical contour of said stent;

each said bend including a trough and a crest, said trough defining a portion of said circumferential element where said circumferential element is more distant from adjacent said circumferential elements than other portions of said circumferential element, said crest defining a portion of said circumferential element where said circumferential element is closer to adjacent circumferential elements than other portions of said circumferential element;

at least one axial element having two extremities and located between at least one pair of adjacent circumferential elements, said extremities each attached to a different one of said pair of adjacent circumferential elements, joining said pair of circumferential elements together;

each said extremity attached to an adjacent one of said circumferential elements at one of said troughs;

at least one linking element having two link ends and located between at least one pair of adjacent circumferential elements, said link ends each attached to a different one of said pair of adjacent circumferential elements at one of said crests; and whereby said axial elements prevent axial contraction of said stent when said stent is expanded radially.

2. The stent of claim 1 wherein said axial elements are of linear elongate form between said extremities and oriented parallel to a central axis of said cylindrical contour of said stent.

3. The stent of claim 2 wherein said circumferential elements have an amplitude defined by an axial distance between one of said troughs and one of said crests, wherein each said circumferential element is spaced from adjacent said circumferential elements by a gap, said gap having a minimum width where said crests of said adjacent circumferential elements are closest to each other and a maximum width where troughs of said adjacent circumferential elements are closest to each other, each said axial element having a length equal to a sum of said amplitude and said minimum width.

4. The stent of claim 1 wherein every trough in every said circumferential element which faces an adjacent circumferential element includes an axial element located therein and attached thereto.

5. The stent of claim 1 wherein said stent includes at least one linking element having two link ends, said linking element located between at least one pair of adjacent circumferential elements, each said link end attached to a different one of said pair of adjacent circumferential elements, joining said pair of circumferential elements together, each said link end attached to said circumferential element at one of said crests.

6. The stent of claim 5 wherein said linking elements are located within gaps between some adjacent said circumferential elements forming said stent and said axial elements are located within gaps between some adjacent said circumferential elements forming said stent, each said gap having at least one element located therein and attaching said circumferential elements adjacent said gap to each other, said gaps provided with said elements in an alternating pattern with said linking elements located in every other said gap and said axial elements located in every other said gap.

7. The stent of claim 6 wherein each said gap includes only similar elements therein, said gaps having said axial elements therein having a larger number of said axial elements than the number of said linking elements located in each said gap having said linking elements therein.

8. The stent of claim 7 wherein each said linking element is arched in a curving manner extending between said crests of adjacent said circumferential elements such that said linking elements span said gap.

9. The stent of claim 7 wherein each said linking element is angled to include a first arm and a second arm joined together by an elbow, said first arm attached to one of said crests of said circumferential element on one side of said gap including said linking element therein and said second arm attached to one of said crests of said circumferential element on an opposite side of said gap in which said linking element is located, said linking element including means to flex about said elbow in a manner allowing a central axis of said stent to flex.

10. The stent of claim 1 wherein each said crest is axially spaced a similar distance from each said trough such that each said circumferential element has a constant amplitude.

11. The stent of claim 10 wherein each said trough and each said crest are bulbous at least when said stent has not yet been radially expanded, such that lateral slots in said gap between adjacent said crests of one said circumferential element are on one side of said gap and adjacent said troughs of two said circumferential elements on opposite sides of said gap are provided with a width which first decreases and then increases as said lateral slot extends away from a center of said gap and toward said circumferential element.

12. The stent of claim 1 wherein each said circumferential element is formed from a series of attached linear segments including linear trough segments oriented perpendicular to a central axis of said cylindrical contour of said stent, crest segments oriented perpendicular to said central axis and spaced axially from said trough segments by an amplitude of said circumferential elements, and inflection segments non-parallel with said trough segments and said crest segments and linking each trough segment to adjacent said crest segments.

13. The stent of claim 1 wherein said first one of said circumferential elements defining said first end of said stent and said second one of said circumferential elements defining said second end of said stent are each formed completely of a material having means to be more opaque when viewed by an imaging device than materials forming other portions of said stent, whereby ends of said stent will more clearly appear when said stent is viewed with the imaging device.

14. A surgical stent for implantation into a body lumen, said stent having a substantially cylindrical contour and being radially expandable, the stent comprising in combination:

a plurality of circumferential elements, each circumferential element encircling said cylindrical contour of said stent;

at least two of said plurality of circumferential elements having an undulating form including at least one trough and at least one crest as said undulating circumferential elements circumscribe said cylindrical contour of said stent;

at least one axial element located between two adjacent said circumferential elements and attached to one of said adjacent circumferential elements at a first junction and to the other of said circumferential elements at a second junction;

wherein said first junction is located spaced from said crests and said second junction is located spaced from said crests; and at least one linking element having two link ends and located between at least one pair of adjacent circumferential elements said link ends each attached to a different one of said pair of adjacent circumferential elements at one of said crests.

15. The surgical stent of claim 14 wherein said plurality of circumferential elements includes at least three circumferential elements including a first end undulating circumferential element located at a first end of said cylindrical contour of said stent, a second end undulating circumferential element located at a second end of said cylindrical contour of said stent, and at least one intermediate circumferential element;

and wherein said stent also includes at least two axial elements including at least one first end axial element and at least one second end axial element, said first end axial element attached to one of said troughs in said first end undulating circumferential element and said second end axial element attached to one of said troughs in said second end undulating circumferential element.

16. The surgical stent of claim 15 wherein each said circumferential element includes said undulating form.

17. The surgical stent of claim 16 wherein each said circumferential element has at least one of said axial elements attached through said first junction to a trough therein and attached through said second junction to a trough of an adjacent said circumferential element.

18. The surgical stent of claim 17 wherein each said intermediate circumferential element has a first side facing said first end undulating circumferential element and a second side facing said second end undulating circumferential element, both said first side and said second side having at least one trough with one of said axial elements attached thereto, said axial element attached thereto also attached to a trough of at least one adjacent said circumferential element.

19. The surgical stent of claim 17 wherein each said intermediate circumferential element has a first side facing said first end undulating circumferential element and a second side facing said second end undulating circumferential element, one said side having at least one trough with one of said axial elements attached thereto, said axial element attached thereto also attached to a trough of at least one adjacent said circumferential element, and one said side having at least one crest with a linking element attached thereto, said linking element also attached to an adjacent said circumferential element.

* * * * *